(12) United States Patent
Brown (10) Patent No.: US 7,108,199 B1
(45) Date of Patent: Sep. 19, 2006

(54) DEVICE FOR DISPENSING LIQUID SCENT

(76) Inventor: Peter M. Brown, P.O. Box 220, Hampden, ME (US) 04444

( * ) Notice: Subject to any disclaimer, the term of this patent is extended or adjusted under 35 U.S.C. 154(b) by 0 days.

(21) Appl. No.: 11/253,332

(22) Filed: Oct. 19, 2005

(51) Int. Cl.
*A01M 31/00* (2006.01)
*A01G 27/00* (2006.01)
*A61L 9/12* (2006.01)
*A61L 9/04* (2006.01)
*B05B 9/03* (2006.01)

(52) U.S. Cl. .................. 239/70; 239/34; 239/127; 239/302; 222/642; 43/1

(58) Field of Classification Search ............ 239/70, 239/34, 127, 302, 37, 40, 46, 47, 51, 67, 239/69, 124, 329; 43/1; 222/642, 650, 420, 222/383.1, 333
See application file for complete search history.

(56) References Cited

U.S. PATENT DOCUMENTS

| | | | |
|---|---|---|---|
| 1,561,039 A | 11/1925 | Walker | |
| 2,692,798 A | 10/1954 | Hicks | |
| 2,722,456 A | 11/1955 | Glessner | |
| 3,042,310 A | 7/1962 | Franke et al. | |
| 3,385,480 A | 5/1968 | Tidwell | |
| 3,672,645 A | 6/1972 | Terrells et al. | |
| 3,941,283 A * | 3/1976 | Garbe | 222/187 |
| 3,958,724 A | 5/1976 | Ordway | |
| 4,723,710 A | 2/1988 | Lucore, II | |
| 4,953,763 A | 9/1990 | Kierum et al. | |
| 4,967,935 A * | 11/1990 | Celest | 222/52 |
| 5,220,741 A | 6/1993 | Burgerson | |
| 5,299,376 A * | 4/1994 | Roberts | 43/2 |
| 5,429,270 A * | 7/1995 | Tumminia | 222/1 |
| 5,449,117 A * | 9/1995 | Muderlak et al. | 239/6 |
| 5,823,390 A * | 10/1998 | Muderlak et al. | 222/38 |
| 6,050,016 A | 4/2000 | Cox | |
| 6,443,434 B1 | 9/2002 | Prather | |

* cited by examiner

*Primary Examiner*—David A. Scherbel
*Assistant Examiner*—Darren Gorman
(74) *Attorney, Agent, or Firm*—Preti Flaherty (57) ABSTRACT

A device for dispensing liquid scent includes a reservoir for containing liquid scent and a reducer tee disposed in an opening in the reservoir. The reducer tee has first, second and third orifices in fluid communication with one another, and the first orifice is located in the reservoir opening so as to be in direct fluid communication with the interior of the reservoir. The device also includes a pump having an inlet and an outlet. A first tube connects the interior of the reservoir to the pump inlet, and a second tube connects the pump outlet to the second orifice. Operation of the pump can be controlled, by a timer for example, so that a predetermined amount of liquid scent is dispensed through the third orifice at a predetermined time. An additional amount of liquid scent is returned to the reservoir via the first orifice.

17 Claims, 9 Drawing Sheets

DEVICE FOR DISPENSING LIQUID SCENT

BACKGROUND OF THE INVENTION

This invention relates generally to devices for dispensing liquid scent and more particularly to such devices that are capable of dispensing liquid scent at precise times and/or in precise amounts.

A common technique used by hunters and others to lure animals to a particular location is to dispense scents in that location. This technique is particularly useful in hunting deer. During mating season, a buck attracts does by making a "scrape," in which the buck paws at the ground and deposits some urine thereon. When a doe is receptive to mating, she will also urinate on the scrape, signaling the buck of her interest. The buck will thus return often to the location of the scrape.

A person may dispense doe-in-heat urine to attract a buck to a particular location, acting on the buck's desire to breed. A person could also dispense buck urine, acting on a buck's dominance instinct. In other words, if a buck has established a scrape and detects the scent of another buck, he will return often to encounter the perceived challenger. In either case, a person typically dispenses the scent on the ground or a tree branch manually using a wick. However, studies have shown that deer have a very acute sense of smell. In some instances, deer have been able to detect human scent for 7–10 days after the human has left the area. Therefore, someone dispensing scent manually is likely to leave behind his or her scent and drive away the animal instead of attracting it.

In response to this problem, devices have been developed that allow scent to be dispensed while the person is not in the area. One such device operates on rising ambient air temperature to create a positive pressure in a reservoir that forces some of the liquid in the reservoir to be dispensed. However, this device does not accurately control the timing and amount of liquid to be dispensed. Another device uses a timing mechanism to actuate a series of rotating gears creating an up and down motion that strokes a manual pump from a sealed reservoir. While this device more accurately controls the timing of dispensing, the size of the reservoir is such that the user must return often to refill, thereby reintroducing human scent to the site. Using a larger reservoir is possible, but that would result in the solids in the liquid scent accumulating at the bottom of the reservoir and undesirable crystallization thereof.

Accordingly, there is a need for liquid scent dispensing device that dispenses scent a precise times over an extended period without excessive human intervention and without solids accumulation and crystallization of the liquid scent.

SUMMARY OF THE INVENTION

The above-mentioned need is met by the present invention, which provides a device for dispensing liquid scent that includes a reservoir for containing liquid scent and a reducer tee disposed in an opening in the reservoir. The reducer tee has first, second and third orifices in fluid communication with one another, and the first orifice is located in the reservoir opening so as to be in direct fluid communication with the interior of the reservoir. The device also includes a pump having an inlet and an outlet. A first tube connects the interior of the reservoir to the pump inlet, and a second tube connects the pump outlet to the second orifice. Operation of the pump can be controlled, by a timer for example, so that a predetermined amount of liquid scent is dispensed through the third orifice at a predetermined time. An additional amount of liquid scent is returned to the reservoir via the first orifice.

The present invention and its advantages over the prior art will be more readily understood upon reading the following detailed description and the appended claims with reference to the accompanying drawings.

DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
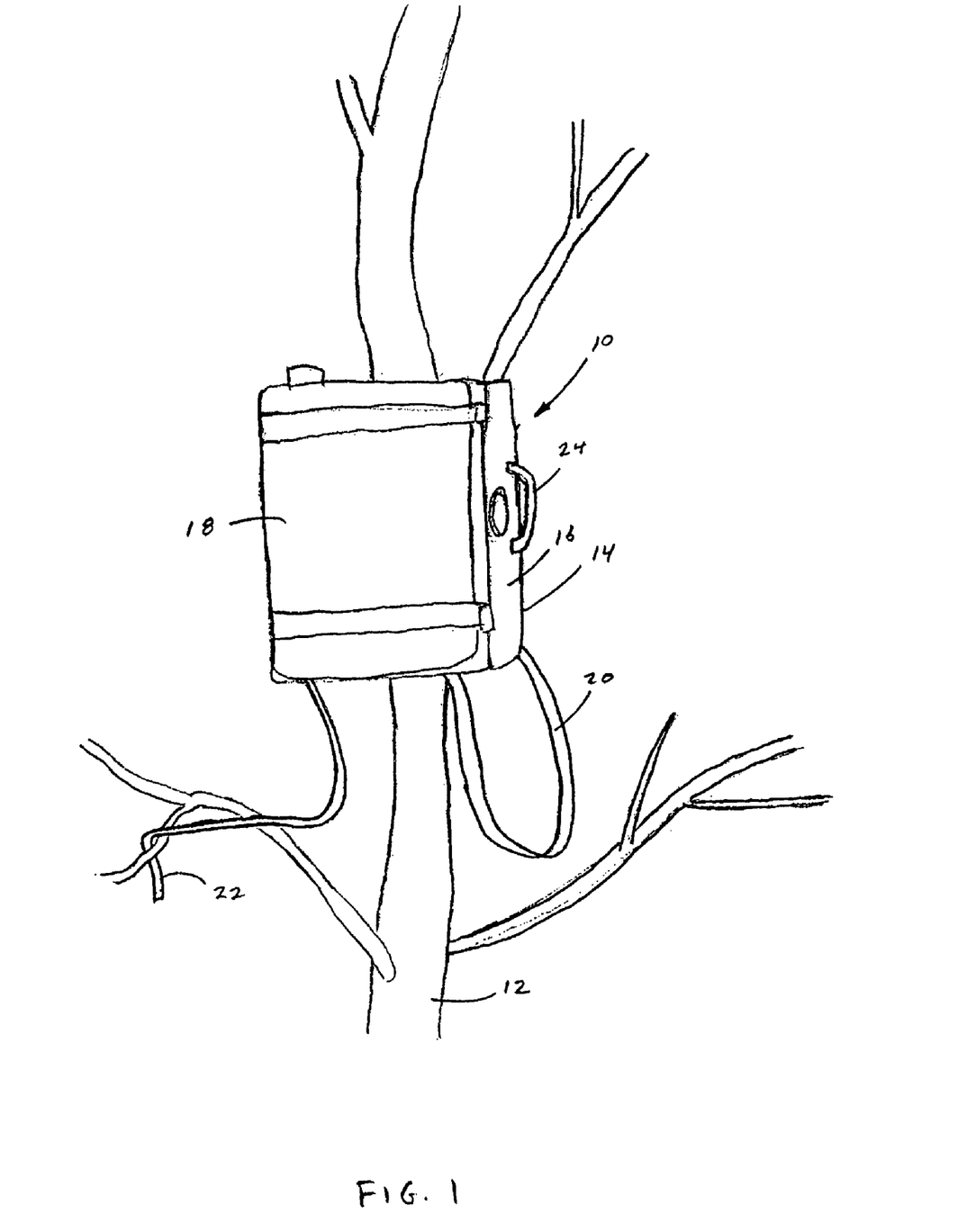
FIG. 1 is a perspective view of a device for dispensing liquid scent mounted in a tree.

Referring to the drawings wherein identical reference numerals denote the same elements throughout the various views, FIG. 1 shows a liquid scent dispensing device 10 mounted to a tree 12. By dispensing predetermined amounts of liquid scent at predetermined times, the device 10 operates to lure animals to the site it is located at. The device 10 includes various elements described in detail below, contained within a watertight housing 14. The housing 14 comprises a box-like casing 16 and a lid 18 hinged to the casing 16 so that the housing 14 can be opened and closed. The lid 18 is normally clasped shut during use (as shown in FIG. 1) thereby creating a substantially watertight enclosure and can be opened by an operator during set up to access various internal elements. A strap 20 is fixed to the backside of the housing 14 for mounting the device 10 to the tree 12 or similar support item. A drip tube 22 protrudes from the bottom of the housing 14, and a handle 24 is optionally attached to the side of the casting 16.

Figure 2:
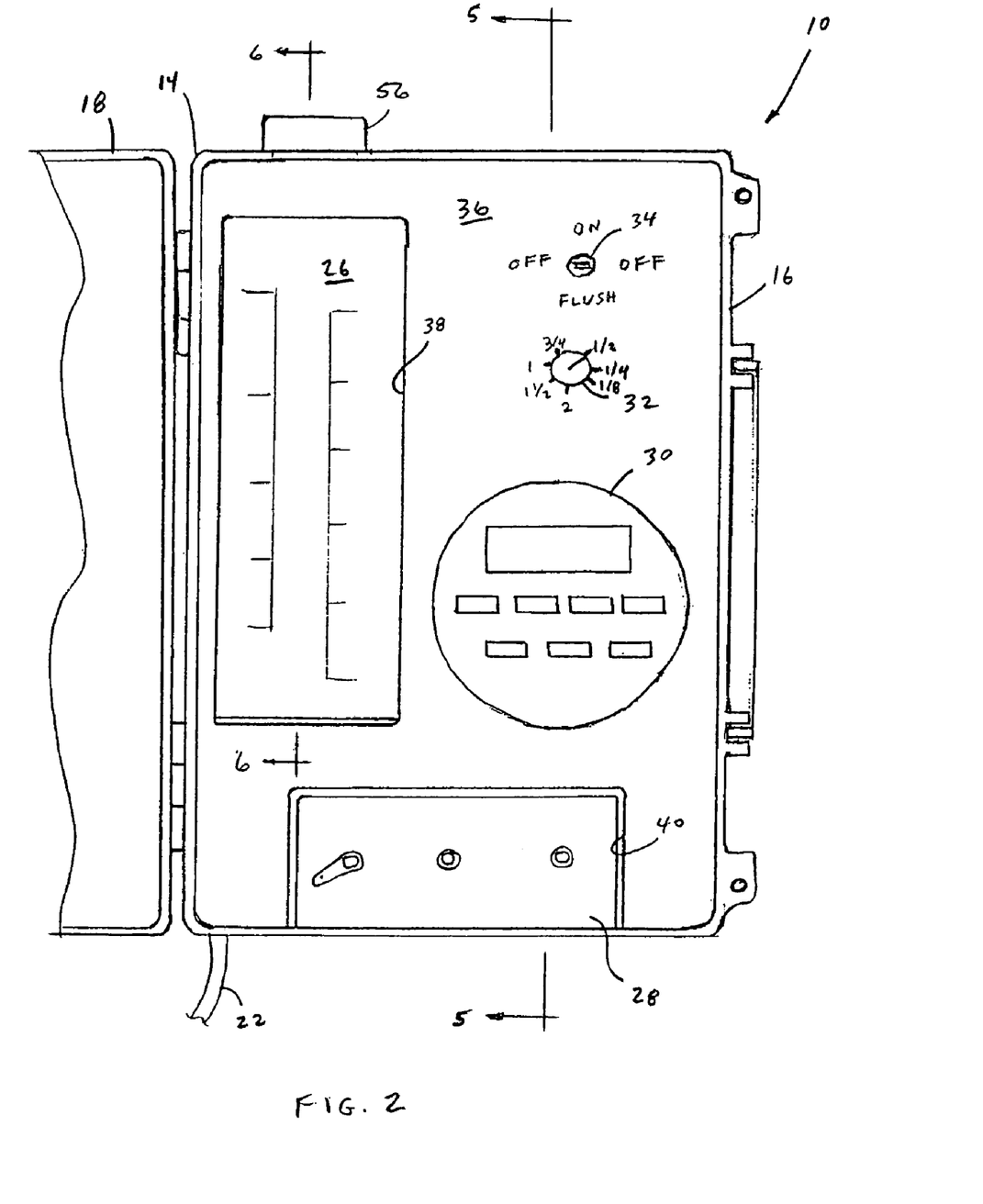
FIG. 2 is a front view of the liquid scent dispensing device with its lid open.
Figure 3:
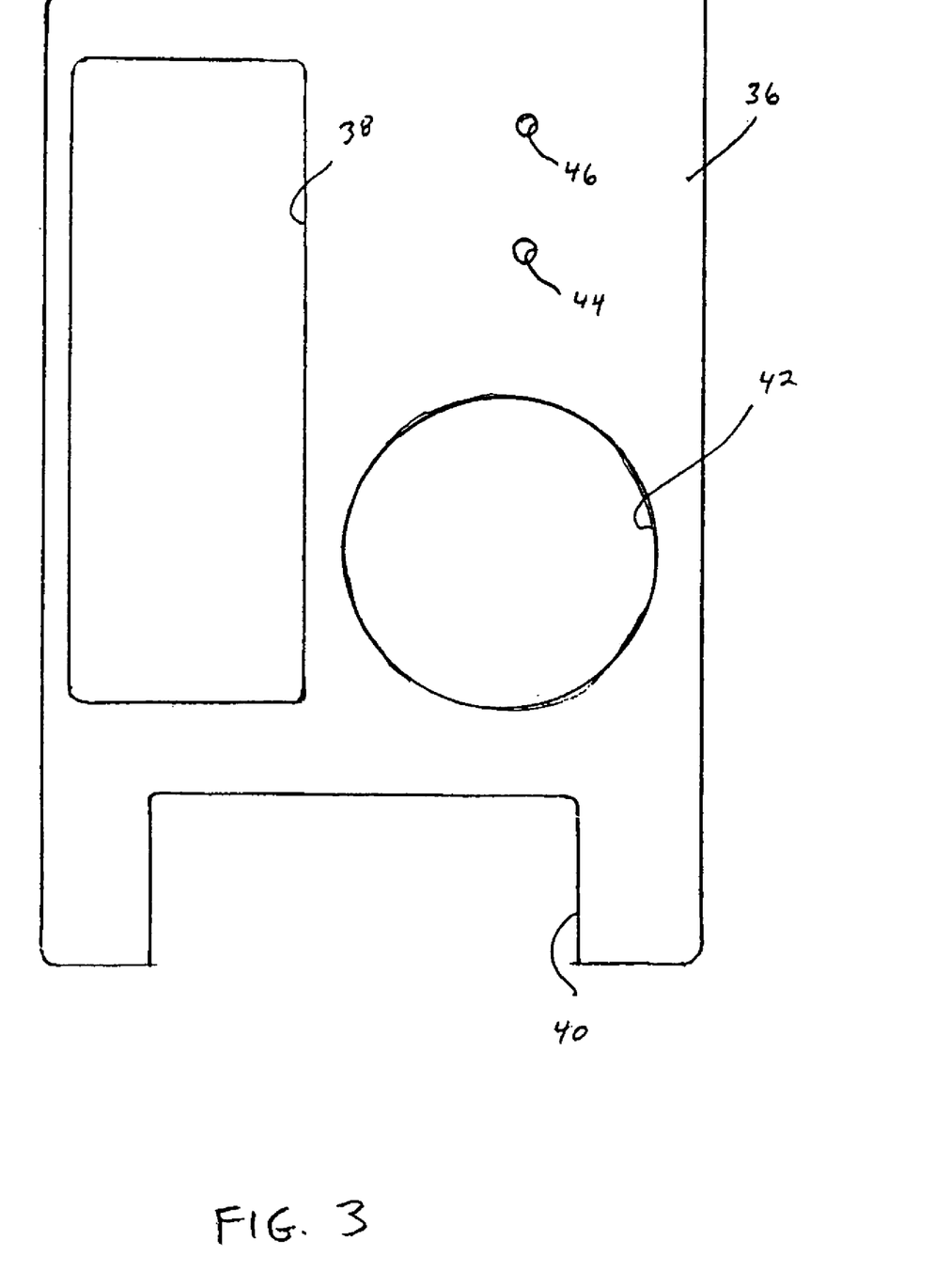
FIG. 3 is a front view of a cover plate from the liquid scent dispensing device.

Turning to FIG. 2, the device 10 is shown with the lid 18 open to reveal the contents of the housing 14, which include a reservoir 26, a power supply 28, a timer 30, a potentiometer 32 and a switch 34. The timer 30, potentiometer 32 and switch 34 are all mounted to the casing 16 via a cover plate 36 that is secured to the upper rim of the casing 16. As seen in FIG. 3, the cover plate 36 has a periphery that matches the shape of the casing upper rim and includes first and second windows 38 and 40. The cover plate 36 further includes a first mounting hole 42 in which the timer 30 is mounted, a second mounting hole 44 in which the potentiometer 32 is mounted, and a third mounting hole 46 in which the switch 34 is mounted. The reservoir 26 and the power supply 28 are disposed within the casing 16, but are visible through the first window 38 and the second window 40, respectfully.

Figure 4:
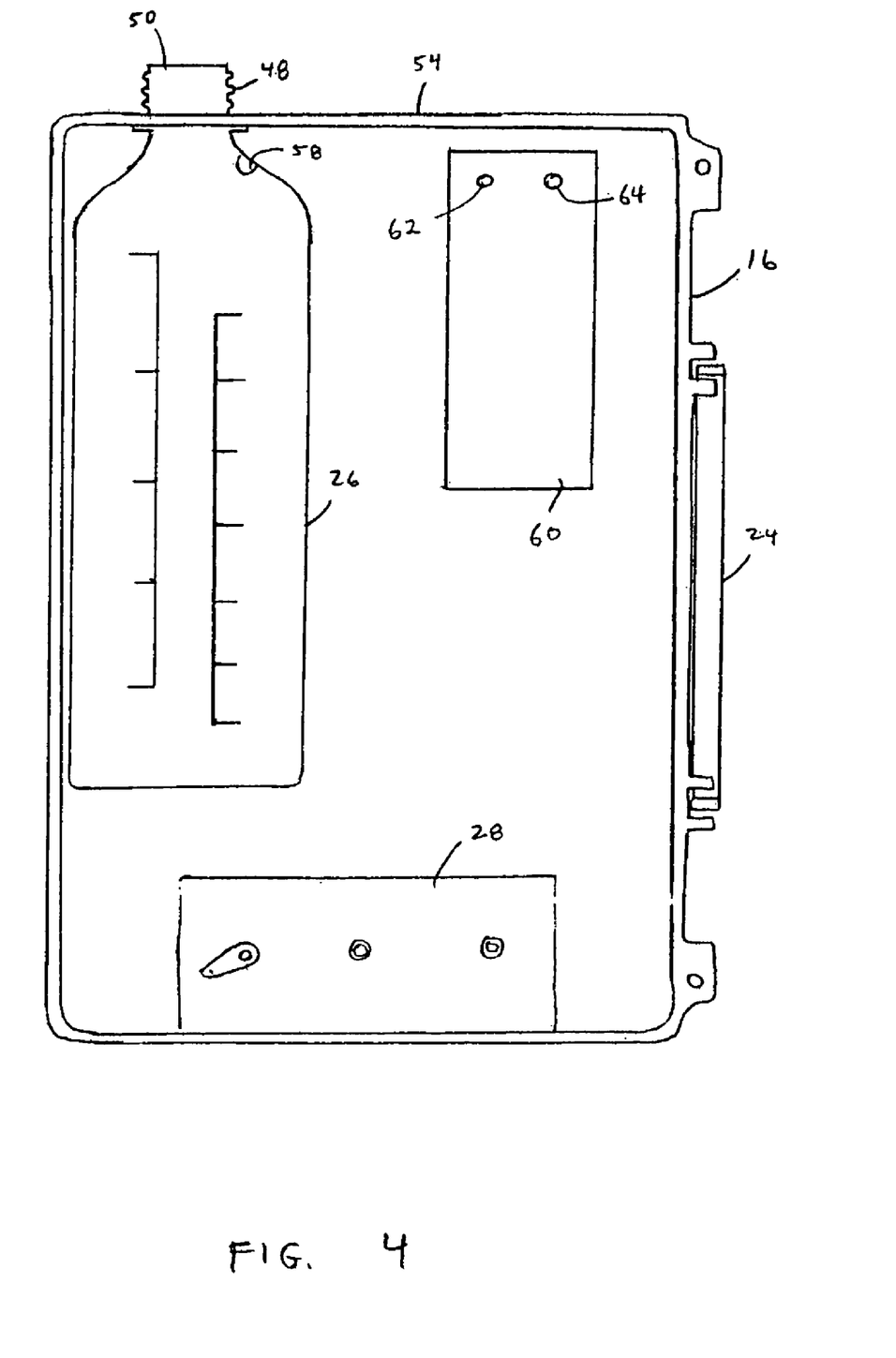
FIG. 4 is a front view of the liquid scent dispensing device with its lid open and the cover plate removed.
Figure 5:
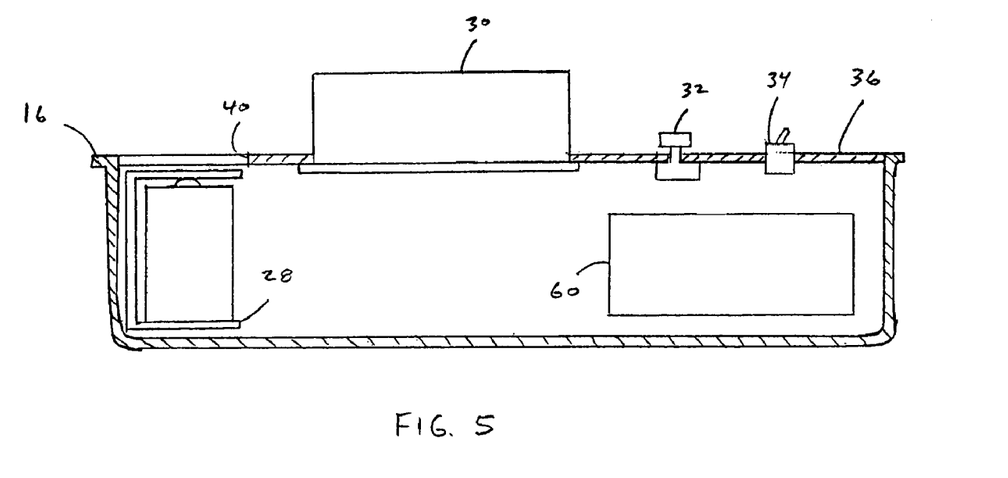
FIG. 5 is a cross-sectional view of the front view of the liquid scent dispensing device with its lid open taken along line 5—5 of FIG. 2.
Figure 6:
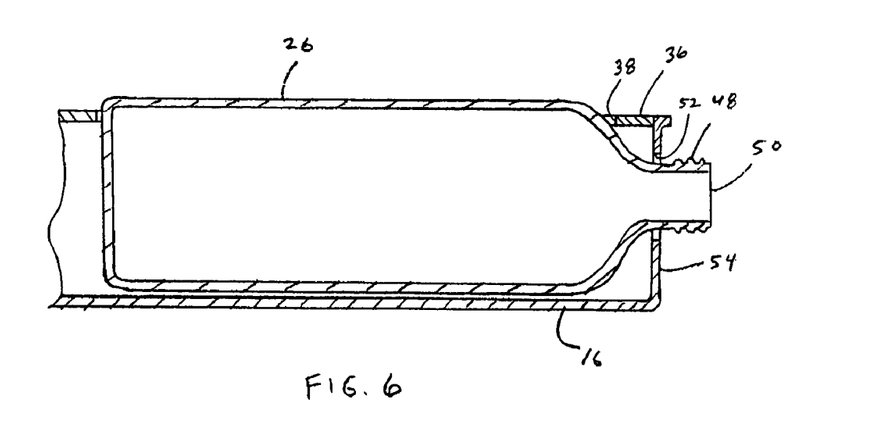
FIG. 6 is a cross-sectional view of the front view of the liquid scent dispensing device with its lid open taken along line 6—6 of FIG. 2.

Referring to FIGS. 4–6, in addition to FIG. 2, the reservoir 26 is provided to hold liquid scent, which can be real or synthetic animal urine. In the illustrated embodiment, the reservoir 26 is a 16-ounce bottle having a cylindrical body and an upwardly extending neck 48 defining a first opening 50, although other size bottles, such as an 8-ounce bottle, can also be used. The bottle is preferably clear or translucent with volume graduations marked on the side thereof. It should be noted that the reservoir 26 is not limited to such a bottle as many types of containers suitable for holding liquid could be used. The reservoir 26 is disposed in the casing 16, largely behind the cover plate 36, but with a portion of the round body protruding slightly through the first window 38 (FIG. 6). The neck 48 protrudes through a hole 52 formed in a side wall 54 of the casing 16. A cap 56 is attached to the neck 48 for covering the first opening 50. A second opening 58 is formed in the reservoir 26, near the base of the neck 48.

The power supply 28 is disposed in the casing 16, substantially behind the cover plate 36 and accessible through the second window 40. In one possible embodiment, the power supply 28 is a battery pack comprising three "D" batteries mounted in a holder and connected in series. Other types of batteries, such as "C" batteries, can alternatively be used. The power supply 28 can be removed via the second window 40 whenever one or more of the batteries need replacement. A pump 60 is also disposed in the casing 16, behind the cover plate 36. In one possible embodiment, the pump 60 is an electric-powered, mini positive displacement plastic vane type pump having an inlet 62 and an outlet 64.

Figure 7:
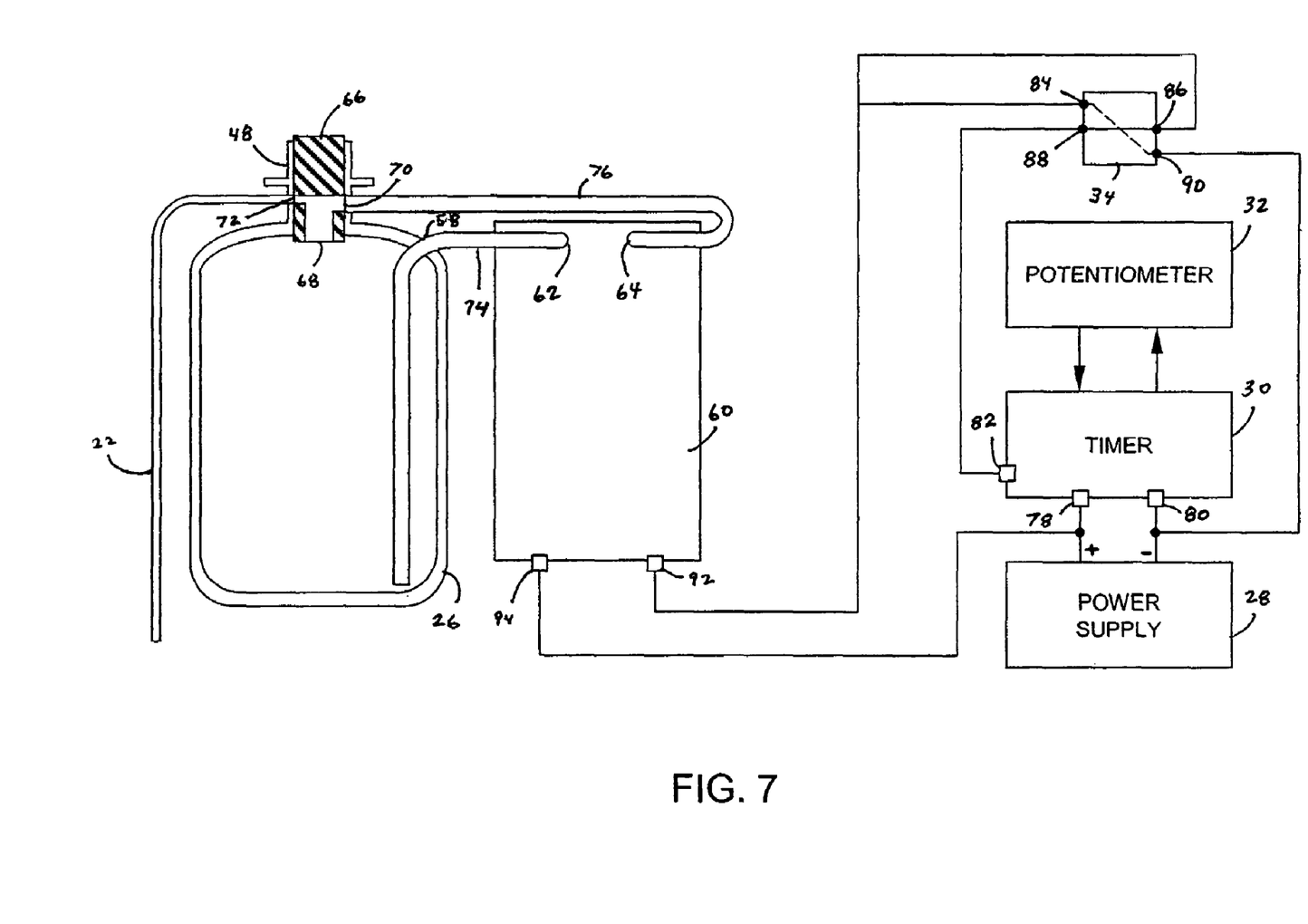
FIG. 7 is a schematic view of the liquid scent dispensing device.

Turning now to FIG. 7, it is seen that a reducer tee 66 having first, second and third orifices 68, 70 and 72 in fluid communication with one another is fitted into the first opening 50 of the reservoir 26, with the first orifice 68 disposed in the neck 48 so as to be in direct fluid communication with the interior of the reservoir 26. The second and third orifices 70 and 72 are located adjacent to respective openings in the side of the neck 48. A suction tube 74 is arranged to extend through the second opening 58 of the reservoir 26 with one end thereof located at the bottom of the reservoir interior and the other end connected to the pump inlet 62. The suction tube 74 thus connects the reservoir interior to the pump inlet 62. A connecting tube 76 is connected between the pump outlet 64 and the second orifice 70 of the reducer tee. A first end of the drip tube 22 is connected to the third orifice 72. As mentioned above, the other end of the drip tube 22 protrudes from the bottom of the housing 14 and is allowed to hang free. With this arrangement, operation of the pump 60 will cause liquid scent to be pumped out of the reservoir 26 via the suction tube 66 to the pump inlet 62, and then pumped to the second orifice 70 via the connecting tube 76. The reducer tee 66 is configured so that the third orifice 72 is smaller than the first and second orifices 68 and 70. Thus, most of the liquid scent delivered to the second orifice 70 through the connecting tube 76 is returned to the reservoir 26 through the first orifice 68, thereby recirculating the contents of the reservoir 26. A small amount of the liquid scent passes through the smaller third orifice 72 to be dispensed through the drip tube 22.

The timer 30 is a programmable timing device that switches on at predetermined times to activate the pump 60. Any suitable timer device can be used; many commercially available timers would be usable. The timer 30 has first and second power terminals 78 and 80 and a common terminal 82. The positive and negative terminals of the power supply 28 are connected to the first and second power terminals 78 and 80, respectively, for powering the timer 30. The operating mode of the device 10 is selected by the switch 34, which is preferably a three-way toggle switch having first, second, third and fourth contacts 84, 86, 88 and 90. The first and second switch contacts 84 and 86 are electrically connected to a first terminal 92 of the pump 60. The third switch contact 88 is electrically connected to the timer common terminal 82, and the fourth switch contact 90 is electrically connected to the negative terminal of the power supply 28. The pump 60 has a second terminal 94 that is electrically connected to the positive terminal of the power supply 28.

The switch 34 is operable between three different positions: on, off and flush. When in the "on" position, the switch 34 creates an electrical connection between the second and third switch contacts 86 and 88, as shown by the solid line in FIG. 7. This creates a circuit between the pump 60, the timer 30 and the power supply 28 so that the pump 30 will be activated at the predetermined times programmed in the timer 30. That is, the timer will establish an electrical connection between the common terminal 82 and the second power terminal 80 (and thus the negative terminal of the power supply 28) at the predetermined times. This will cause the pump 60 to be activated because the common terminal 82 is connected to the first pump terminal 92 via the switch 34. The potentiometer 32, which can be a one-mega ohm potentiometer, is connected to the timer 30 for controlling the amount of liquid scent that is dispensed during each activation. Adjusting the potentiometer 32 alters the pump delay time so as to control the amount of liquid scent dispensed. In the illustrated embodiment, by way of example, the potentiometer 32 can be set to produce ⅛-, ¼-, ½-, ¾-, 1-, 1½-, or 2-ounce amounts.

When in the "flush" position, the switch 34 creates an electrical connection between the first and fourth switch contacts 84 and 90, as shown by the dashed line in FIG. 7. This completes a circuit between the pump 60 and the power supply 28, bypassing the timer 30. Thus, the pump 60 will operate continuously to pump fluid scent form the reservoir 26. This setting can thus be used to prime the device 10. None of the switch contacts are electrically connected when the switch 34 is in its "off" position. The pump 60 is accordingly disconnected from the power supply 28, thereby preventing pump operation all together.

In use, the reservoir 26 is filled with liquid scent by removing the reducer tee 66 and pouring the liquid scent through the first opening 50. As mentioned above, the liquid scent is preferably real or synthetic animal urine. The reducer tee 66 is then replaced in the first opening 50. The device 10 is then mounted to a tree or other support structure at the desired location. The drip tube 22 is arranged to hang so that its outer end is pointing downward (see FIG. 1). The user can then open the lid 18 to set up the device 10. If needed, the switch 34 can be briefly set to the "flush" position to prime the pump 60. The user then programs the timer 30 so as to activate the pump 60 at the desired time or times. The timer 30 can be programmed for single or multiple activations on a given day or days. For example, the timer 30 can be programmed to activate the pump 60 every day of the week at a selected time or times. Or the timer 30 can be programmed to activate the pump 60 only on selected days of the week, such as Monday, Wednesday and Friday, or Friday through Sunday. This allows the user to designate certain times and days to more accurately condition the animal to return to the location at these times. The user also adjusts the potentiometer 32 to set the desired amount of liquid scent to be dispensed for each activation. With the timer 30 and potentiometer 32 set, the user sets the switch 34 to the "on" position and closes the lid 18. The device 10 is now ready for operation and the user can leave the location.

At the programmed times, the timer 30 will cause the pump 60 to be activated. The pump 60 will pump liquid scent from the reservoir 26 via the suction tube 66 to the pump inlet 62, and then to the second orifice 70 of the reducer tee 66 via the connecting tube 76. A relatively large amount of this liquid scent is returned to the reservoir 26 through the first orifice 68, while the rest of the liquid scent passes through the smaller third orifice 72 to be dispensed to the environment through the drip tube 22. Returning a large portion of the liquid scent to the reservoir 26 through the first orifice 68 circulates the liquid scent to minimize accumulation of solids and crystallization of the liquid scent. This provides a more uniform chemical composition of the liquid scent that is dispensed.

Figure 8:
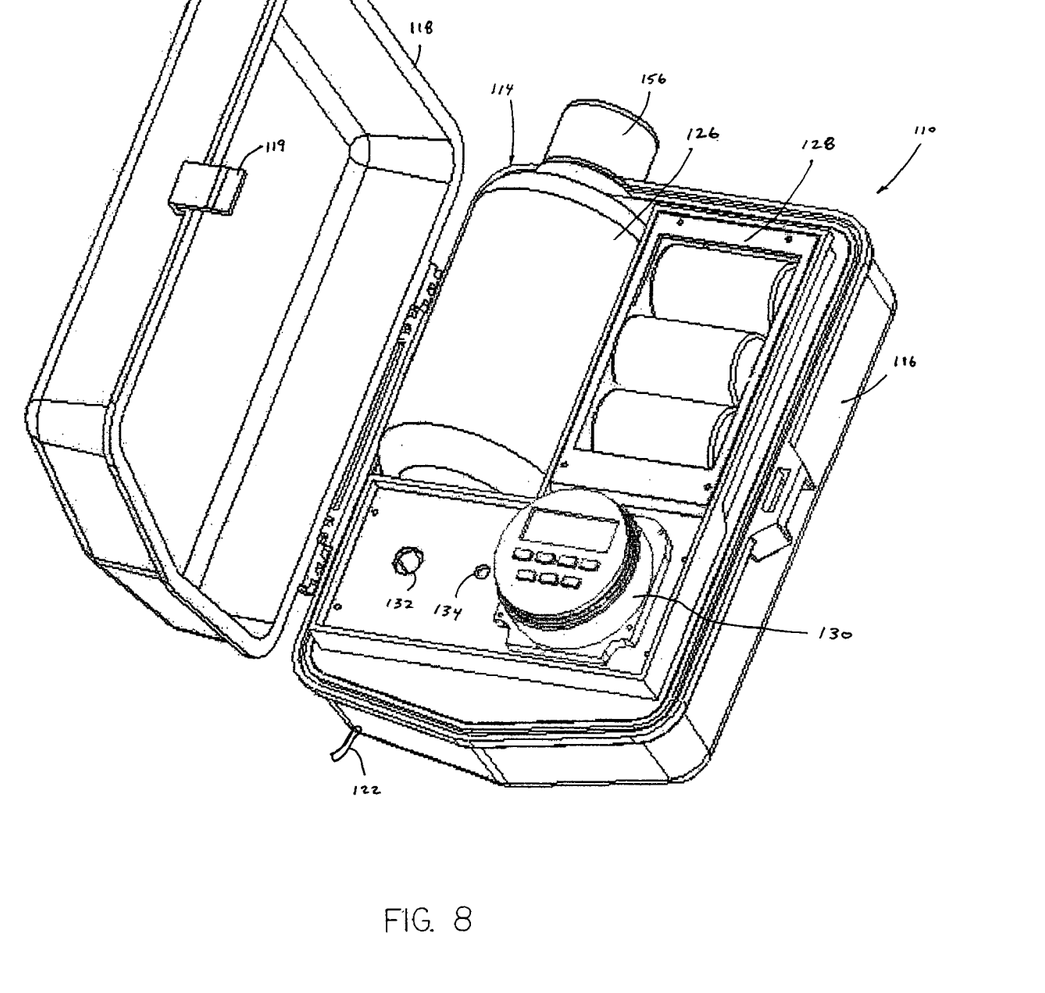
FIG. 8 is a perspective view of a second embodiment of a device for dispensing liquid scent.
Figure 9:
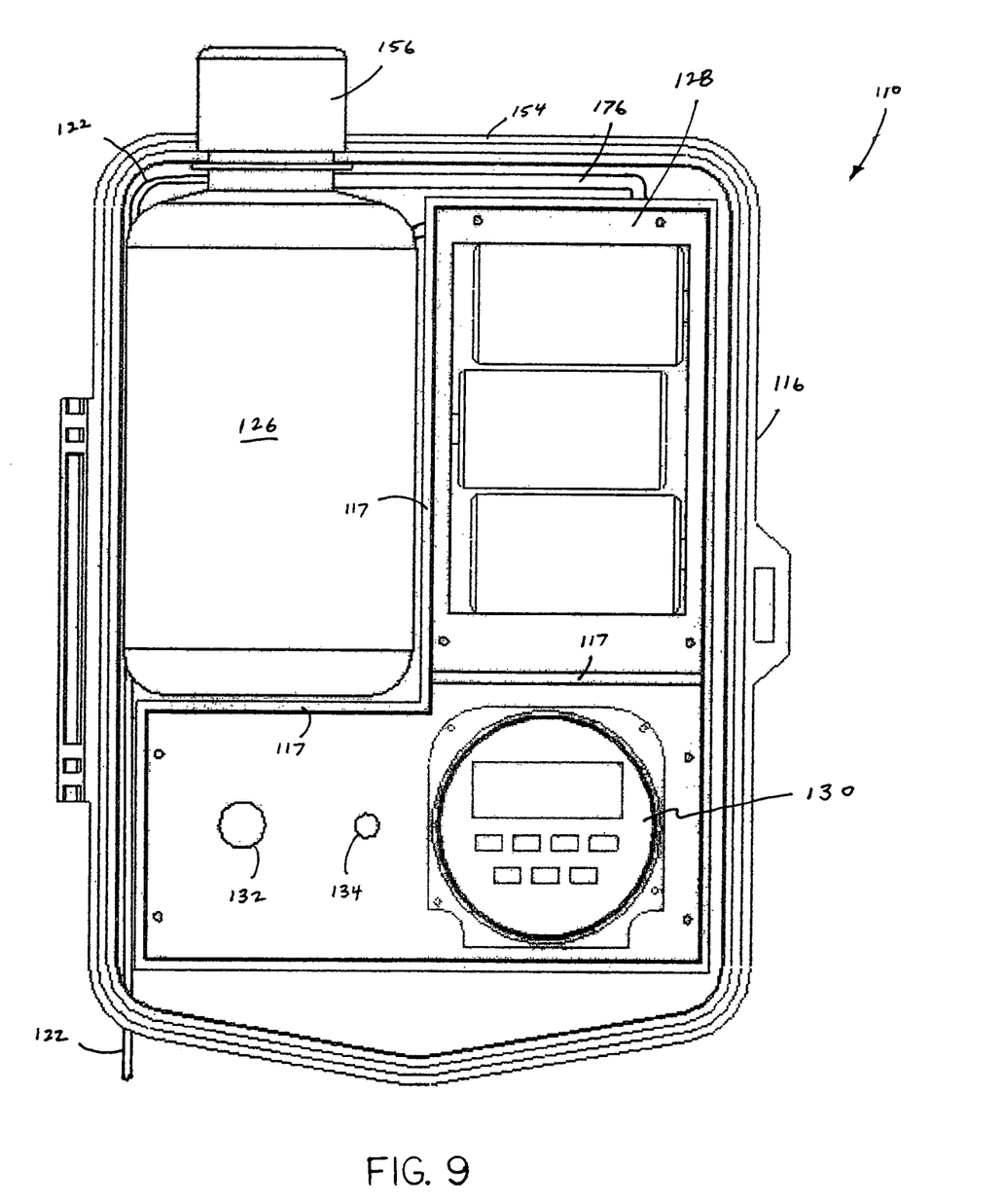
FIG. 9 is a front view of the liquid scent dispensing device of FIG. 8 with its lid and cover plate removed.
Figure 10:
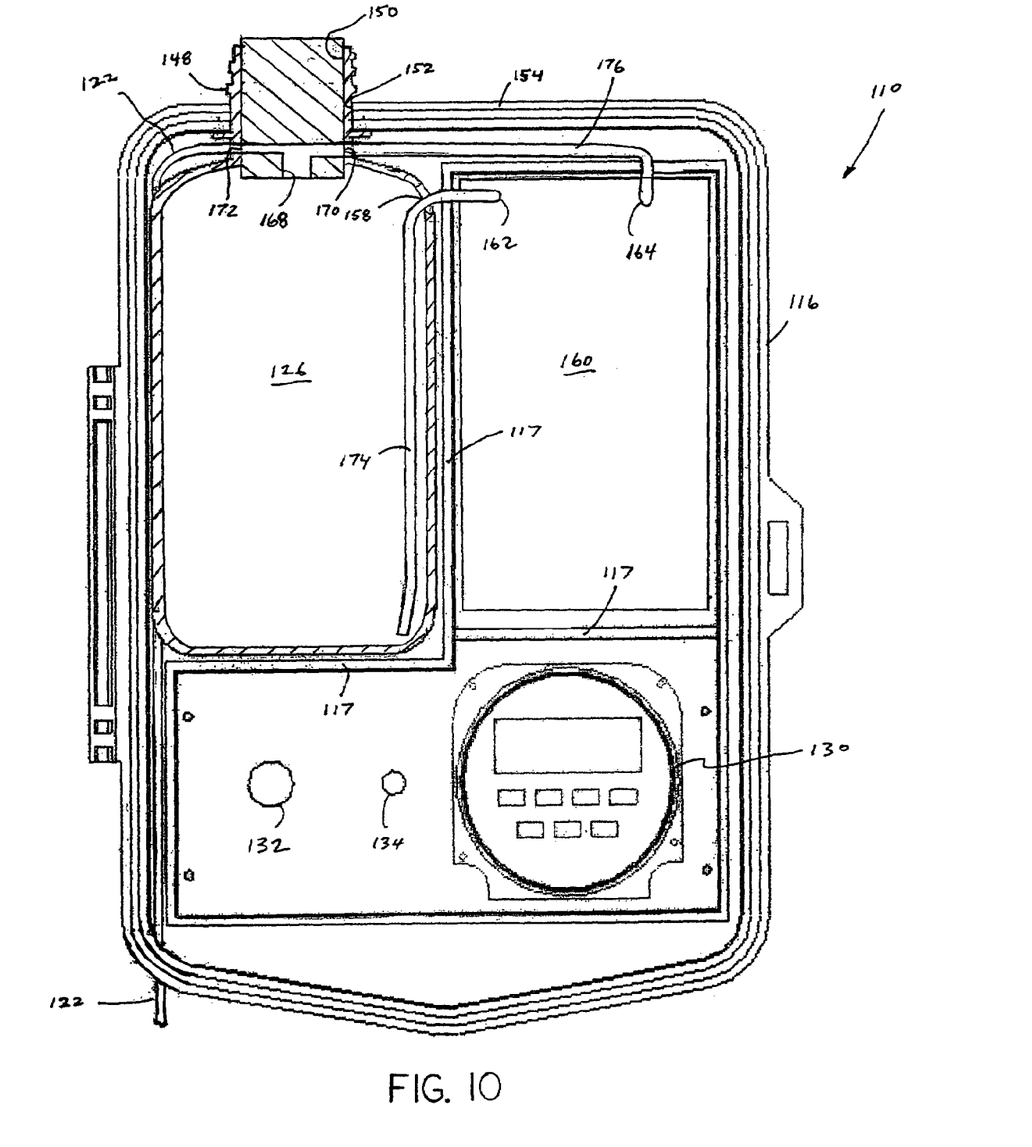
FIG. 10 is a front view of the liquid scent dispensing device of FIG. 9 with its power supply removed.

Referring now to FIGS. 8–10, a liquid scent dispensing device 110 in accordance with a second embodiment is shown. Like the first embodiment, the device 110 includes various elements described in detail below, contained within a watertight housing 114. The elements of this second embodiment are essentially the same as the elements of the first embodiment but are arranged in the housing 114 in a different manner. The housing 114 comprises a box-like casing 116 and a lid 118 hinged to the casing 116 so that the housing 114 can be opened and closed. The lid 118 is normally clasped shut during use by a clasp 119 thereby creating a substantially watertight enclosure and can be opened by an operator during set up to access various internal elements. A strap (not shown) or similar means can be provided for mounting the device 110 to an object such as a tree or the like. A drip tube 122 protrudes from the bottom of the housing 114.

The device 110 includes a reservoir 126, a power supply 128, a timer 130, a potentiometer 132, a switch 134 and a pump 160 contained within the housing 114. The casing 116 includes internal partitions 117 that divide the casing 116 into a number of compartments. The reservoir 126 is disposed in a first compartment located in the upper left corner of the casing 116, as viewed in the Figures. The power supply 128 and the pump 160 are both disposed in a second compartment located in the upper right corner of the casing 116 with the power supply 128 positioned on top of the pump 160. (FIG. 10 shows the device 110 with the power supply 128 removed so as to reveal the pump 160.) The timer 130, potentiometer 132 and switch 134 are located in the lower section of the casing 116. A cover plate (not shown) is secured to the upper rim of the casing 116 and has a recess formed therein for enclosing the power supply 128 in a watertight manner to protect against corrosive liquid scent in the event of a leak.

The reservoir 126 is provided to hold liquid scent, which can be real or synthetic animal urine. In the illustrated embodiment, the reservoir 126 is a 16-ounce bottle having a cylindrical body and an upwardly extending neck 148 defining a first opening 150. The bottle is preferably clear or translucent with volume graduations marked on the side thereof. It should be noted that the reservoir 126 is not limited to such a bottle as many types of containers suitable for holding liquid could be used. The reservoir 126 is disposed in the casing 116, with a portion of the round body protruding slightly through an opening in the cover plate. The neck 148 protrudes through a hole 152 formed in a sidewall 154 of the casing 116. A cap 156 is attached to the neck 148 for covering the first opening 150. A second opening 158 is formed in the reservoir 126, near the base of the neck 148.

In one possible embodiment, the power supply 128 is a battery pack comprising three "D" batteries mounted in a holder and connected in series. The power supply 128 can be removed whenever one or more of the batteries need replacement. As mentioned above, the pump 160 is located in the casing 116, behind the power supply 128. In one possible embodiment, the pump 160 is an electric-powered, mini positive displacement plastic vane type pump having an inlet 162 and an outlet 164.

Referring to FIG. 10, it is seen that a reducer tee 166 having first, second and third orifices 168, 170 and 172 in fluid communication with one another is fitted into the first opening 150 of the reservoir 126, with the first orifice 168 disposed in the neck 148 so as to be in direct fluid communication with the interior of the reservoir 126. The second and third orifices 170 and 172 are located adjacent to respective openings in the side of the neck 148. A suction tube 174 is arranged to extend through the second opening 158 of the reservoir 126 with one end thereof located at the bottom of the reservoir interior and the other end connected to the pump inlet 162. The suction tube 174 thus connects the reservoir interior to the pump inlet 162. A connecting tube 176 is connected between the pump outlet 164 and the second orifice 170 of the reducer tee. A first end of the drip tube 122 is connected to the third orifice 172. As mentioned above, the other end of the drip tube 122 protrudes from the bottom of the housing 114 and is allowed to hang free. With this arrangement, operation of the pump 160 will cause liquid scent to be pumped out of the reservoir 126 via the suction tube 166 to the pump inlet 162, and then pumped to the second orifice 170 via the connecting tube 176. The reducer tee 166 is configured so that the third orifice 172 is smaller than the first and second orifices 168 and 170. Thus, most of the liquid scent delivered to the second orifice 170 through the connecting tube 176 is returned to the reservoir 126 through the first orifice 168, thereby recirculating the contents of the reservoir 126. A small amount of the liquid scent passes through the smaller third orifice 172 to be dispensed through the drip tube 122.

The timer 130, the potentiometer 132 and the switch 134 are electrically connected with the power supply 128 and the pump 160 in the same manner as that described above in connection with the first embodiment. Operation of the device 110 is similar to the operation of the first embodiment and is thus not repeated here.

While specific embodiments of the present invention have been described, it will be apparent to those skilled in the art that various modifications thereto can be made without departing from the spirit and scope of the invention as defined in the appended claims.

What is claimed is:

1. A device for dispensing liquid scent, said device comprising:
   a reservoir for containing liquid scent, said reservoir having a first opening;
   a reducer tee disposed in said first opening, said reducer tee having first, second and third orifices in fluid communication with one another, said first orifice being located in said first opening so as to be in direct fluid communication with the interior of said reservoir;

a pump having an inlet and an outlet;

a first tube connecting the interior of said reservoir to said pump inlet;

a second tube connecting said pump outlet to said second orifice; and means for controlling said pump so that a predetermined amount of liquid scent is dispensed through said third orifice at a predetermined time.

2. The device of claim 1 wherein said means for controlling said pump includes a timer that allows said pump to be activated at said predetermined time.

3. The device of claim 2 wherein said means for controlling said pump further includes a potentiometer connected to said timer.

4. The device of claim 3 further comprising a power supply for supplying power to said pump and said timer.

5. The device of claim 4 further comprising a switch having first, second and third positions, wherein said switch creates a circuit between said timer, said pump and said power supply when in said first position, wherein said switch creates a circuit between said pump and said power supply when in said second position, and wherein said pump and said power supply are disconnected when said switch is in said third position.

6. The device of claim 1 wherein said third orifice is smaller than said first and second orifices.

7. The device of claim 1 further comprising a drip tube connected to said third orifice.

8. The device of claim 1 wherein said reservoir has a second opening and said first tube extends through said second opening.

9. A device for dispensing liquid scent, said device comprising:

a housing;

a reservoir for containing liquid scent disposed in said housing, said reservoir having a first opening;

a reducer tee disposed in said first opening, said reducer tee having first, second and third orifices in fluid communication with one another, said first orifice being located in said first opening so as to be in direct fluid communication with the interior of said reservoir;

a pump disposed in said housing and having an inlet and an outlet;

a first tube connecting the interior of said reservoir to said pump inlet;

a second tube connecting said pump outlet to said second orifice; and means for controlling said pump so that a predetermined amount of liquid scent is dispensed through said third orifice at a predetermined time.

10. The device of claim 9 wherein said housing has a lid that provides access to the interior of said housing when open and creates a substantially watertight enclosure when closed.

11. The device of claim 9 wherein said means for controlling said pump includes a timer that allows said pump to be activated at said predetermined time.

12. The device of claim 11 wherein said means for controlling said pump further includes a potentiometer connected to said timer.

13. The device of claim 11 further comprising a power supply for supplying power to said pump and said timer.

14. The device of claim 13 further comprising a switch having first, second and third positions, wherein said switch creates a circuit between said timer, said pump and said power supply when in said first position, wherein said switch creates a circuit between said pump and said power supply when in said second position, and wherein said pump and said power supply are disconnected when said switch is in said third position.

15. The device of claim 9 wherein said third orifice is smaller than said first and second orifices.

16. The device of claim 9 further comprising a drip tube connected to said third orifice.

17. The device of claim 9 wherein said reservoir has a second opening and said first tube extends through said second opening.

* * * * *